US00PP35263P3

(12) United States Plant Patent
Holtmaat

(10) Patent No.: US PP35,263 P3
(45) Date of Patent: Jul. 11, 2023

(54) ***HEUCHERA* PLANT NAMED 'TONCKA 377'**

(50) Latin Name: ***Heuchera* hybrid**
Varietal Denomination: Toncka 377

(71) Applicant: Henricus Maria Joseph Holtmaat, Zuidwolde (NL)

(72) Inventor: Henricus Maria Joseph Holtmaat, Zuidwolde (NL)

(73) Assignee: AB KWEKERSRECHTEN B.V., Zuidwolde (NL)

( * ) Notice: Subject to any disclaimer, the term of this patent is extended or adjusted under 35 U.S.C. 154(b) by 0 days.

(21) Appl. No.: 17/961,712

(22) Filed: Oct. 7, 2022

(65) Prior Publication Data

US 2023/0157191 P1 May 18, 2023

(30) Foreign Application Priority Data

Nov. 15, 2021 (QZ) ..... PBR 20212932

(51) Int. Cl.
*A01H 5/12* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./263.1, 440
See application file for complete search history.

(56) References Cited

U.S. PATENT DOCUMENTS

PP18,009 P2 * 9/2007 Egger ..... A01H 6/80
Plt./440

* cited by examiner

*Primary Examiner* — Karen M Redden
(74) *Attorney, Agent, or Firm* — Penny J Aguirre

(57) ABSTRACT

A new cultivar of *Heuchera* plant named 'Toncka 377' that is characterized by its leaves that have glossy surfaces, its leaves that are grey-green in color with dark green veins, its flowers that are clear red-purple in color, and its very floriferous blooming habit.

2 Drawing Sheets

Botanical classification: *Heuchera* hybrid.
Cultivar designation: 'Toncka 377'.

CROSS REFERENCE TO A RELATED APPLICATION

This application claims priority to European Community Plant Variety Office (CPVO) Plant Breeder's Rights Application No. No. 2021/2932, filed Nov. 15, 2021. The Applicant received the information for the Plant breeders' rights application directly from the Inventor.

BACKGROUND OF THE INVENTION

The present invention relates to a new and distinct cultivar of *Heuchera* of hybrid origin, botanically known as *Heuchera* 'Toncka 377' and is hereinafter referred to by its cultivar name 'Toncka 377'.

The new cultivar was discovered as a chance seedling in a trial field by the Inventor in Zuidwolde, The Netherlands in July of 2019. The source of the seedling was from seed collected in 2019 from open pollinated plants in a trial field that contained numerous unnamed and unpatented proprietary *Heuchera* seedlings from the Inventor's breeding program. The parentage of 'Toncka 377' is therefore unknown.

Asexual propagation of the new cultivar was first accomplished under the direction of the Inventor by tissue culture initiated from meristem tissue in September of 2020 in Heerhugowaard, The Netherlands. Asexual propagation of the new cultivar by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Toncka 377' as a new and unique cultivar of *Heuchera*.

1. 'Toncka 377' exhibits leaves that have glossy surfaces.
2. 'Toncka 377' exhibits leaves that are grey-green in color with dark green veins.
3. 'Toncka 377' exhibits flowers that are clear red-purple in color.
4. 'Toncka 377' exhibits a very floriferous blooming habit.

'Toncka 377' can be most closely compared to the *Heuchera* cultivars 'Tokyo' (U.S. Plant Pat. No. 27,363) and 'Peppermint Spice' (U.S. Plant Pat. No. 18,009). 'Tokyo' is similar to 'Toncka 377' in leaf size. 'Tokya' differs from 'Toncka 377' in having foliage that is greener in color and flowers that are red in color. 'Peppermint Spice' is similar to 'Toncka 377' in leaf size and flower color. 'Peppermint Spice' differs from 'Toncka 377' in having foliage that are more grey in color and flowers that are smaller in size and in producing less inflorescences.

BRIEF DESCRIPTION OF THE DRAWINGS

The accompanying color photographs illustrate the overall appearance and distinct characteristics of the new *Heuchera*. The photographs were taken of a plant 18 months in age of the new cultivar as grown outdoors in a 19-cm containers in Zuidwolde, The Netherlands.

The photograph in FIG. 1 provides a side view of the plant of 'Toncka 377' in bloom.

Figure 1:
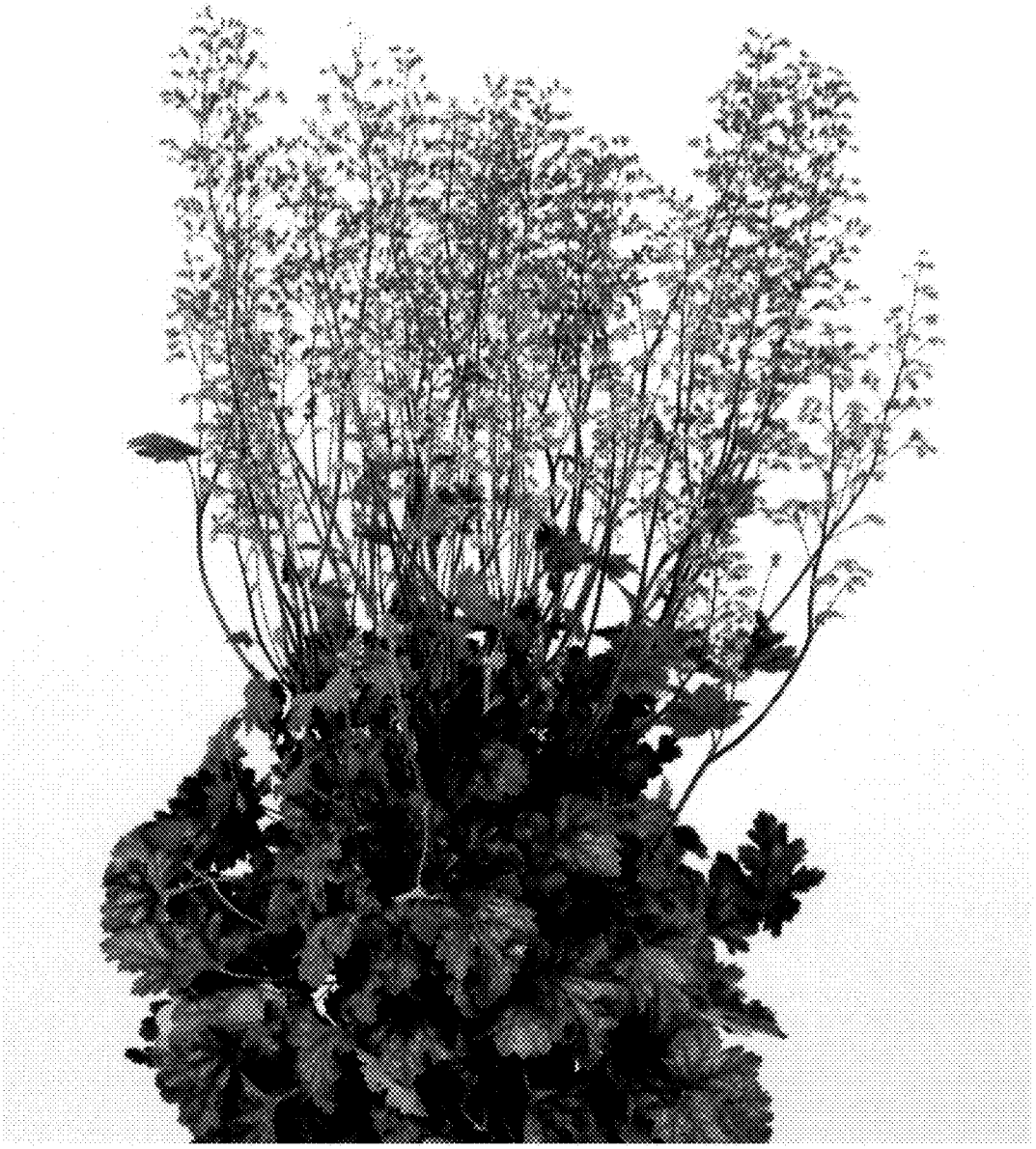
Figure 2:
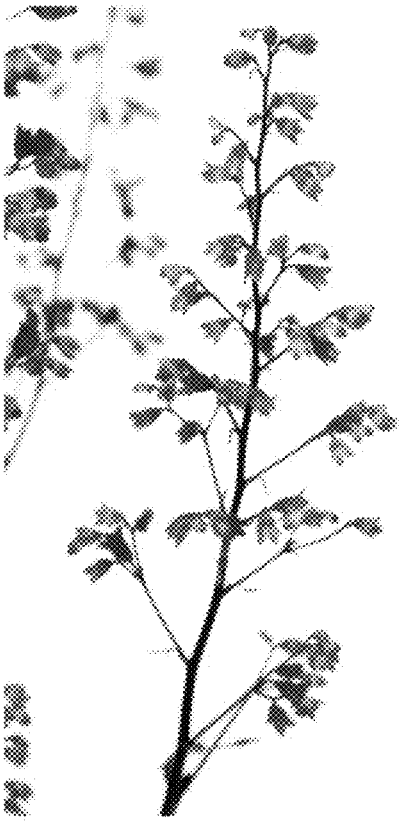

The photograph in FIG. 2 provides a close up of an inflorescence of 'Toncka 377'.

Figure 3:
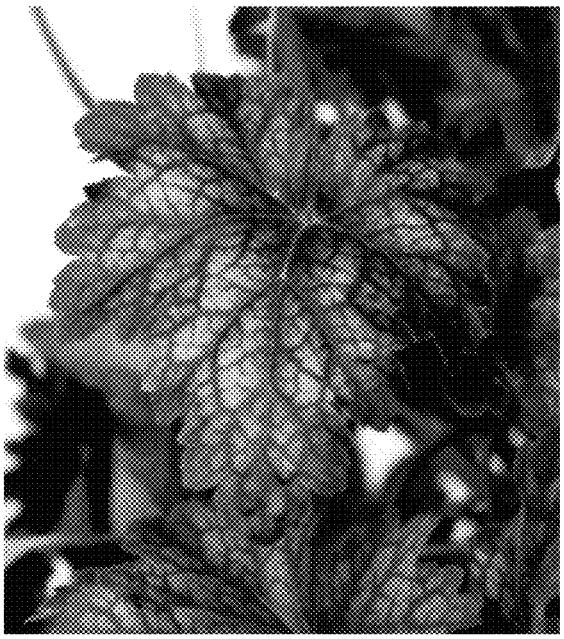

The photograph in FIG. 3 provides a close up view of the foliage of 'Toncka 377'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 18 month-old plants of the new cultivar as grown outdoors in 19-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—10 weeks, midsummer to late summer in The Netherlands.

*Plant type*.—Herbaceous perennial.

*Plant habit*.—Globular with inflorescences held above the foliage.

*Height and spread*.—An average of 30 cm in height (soil level to top of foliar plane), average of 75 cm in height (soil level to top of floral plane) and 65 cm in spread as an 18 month-old plant.

*Cold hardiness*.—At least in U.S.D.A. Zone 3.

*Diseases and pests*.—No susceptibility or resistance to pests or diseases has been observed.

*Root description*.—Fibrous roots on woody rootstalks, 158D in color.

*Propagation*.—Tissue culture.

*Root development*.—An average of 3 weeks for root initiation and 6 weeks to produce a rooted cutting.

*Growth rate*.—Vigorous.

*Branching habit*.—Flowering stems emerge from basal rosette, an average of 50 rosettes per plant, no lateral branches.

Foliage description:

*Leaf shape*.—Broad ovate in outline, slightly concave.

*Leaf division*.—Simple.

*Leaf base*.—Hastate, lobes free to touching.

*Leaf apex*.—Short and abruptly acute.

*Leaf venation*.—Laciniate, upper surface 136A and 139A, lower surface 145A.

*Leaf margins*.—Crenate to crenate-serrate with abruptly acute tips on each tooth, slightly to moderately coarsely undulate.

*Leaf attachment*.—Petiolate.

*Leaf arrangement*.—Alternate in basal rosettes.

*Leaf lobes*.—Lobed, an average of 7 to 9 lobes, medium in depth, divergent, lobe margins free to touching.

*Leaf surface*.—Upper surface; smooth, pubescent, moderately velvety, matte, non-rugose, lower surface; smooth, matte, non-rugose, both surfaces moderately covered with very short strigose hairs 0.35 mm in length and closest to NN155D in color; hard to measure color based on sparseness and the small size.

*Leaf color*.—Young upper surface; 144A, tips 137B, young lower surface; 138B, mature upper surface; 191B and 191C, mature lower surface; 191A.

*Leaf size*.—An average of 10.8 cm in length and 9.8 cm in width.

*Leaf quantity*.—An average of 8 per basal rosette.

*Petioles*.—An average of 19.4 cm in length and 3 mm in diameter, medium strength, both surfaces slightly glossy, both surfaces 144A in color, moderately covered with short soft hairs, average of 0.75 mm in length, hairs on both sides closest to NN155D in color; hard to measure color based on sparseness and the small size.

*Stipules*.—Leafy stipule at the base of each leaf, average 2.3 cm in length, average 6 mm in width, acute tip, 150D in color.

Flower description:

*Inflorescence type*.—Numerous small bell-shaped flowers arranged on panicles on peduncles emerging from a basal rosette.

*Inflorescence size*.—An average of 34.5 cm in height and 9.1 cm in diameter.

*Inflorescence number*.—An average of 50.

*Flower fragrance*.—None.

*Flower quantity*.—Average of 275 flowers per flowering stem, 11,500 per plant.

*Flower lastingness*.—Average of one week.

*Flower buds*.—Obovate in shape, an average of 6 mm in length and 3 mm in diameter, color; 53C, lower half 54B, surface is matte and densely covered with very short glandular hairs; an average of 0.3 mm in length and too small to measure color.

*Flower aspect*.—Slightly outward to nodding.

*Flower type*.—Single, campanulate.

*Flower size*.—Average of 7 mm in height and diameter.

*Petals*.—Average of 5, rotate arrangement and implanted in the hypanthium at base, oblanceolate in shape, margin is entire, apex is acute, base is long acuminate, upper and lower surface is glabrous, smooth and matte, an average of 4 mm in length and 1 mm in width, color when opening upper and lower surface; 62C, when fully open 62C to 62D.

*Calyx*.—Campanulate, sepals fused to hypanthium, 8 mm in length, 7 mm in diameter.

*Sepals*.—An average of 5, lower 44% fused into campanulate hypanthium, ovate in shape, an average of 8 mm in length and 3 mm in width, margin is entire and fused into hypanthium, apex is acute, color; when opening upper surface 53D, base 54C, fused part 173B to 173C, when opening lower surface; 54A, base 54D, when fully open upper surface; 53D, base 54D, fused part 173B, fully open lower surface; 54A, base 54D, both surfaces are matte and densely covered with very short glandular hairs an average of 0.2 mm in length and to small to measure color.

*Peduncle*.—An average of 65.9 cm in length and 4 mm in diameter, color; 183A and 187A, primary flower aspect 65° to horizontal, secondary peduncle aspect to main peduncle 40°, moderate in strength, surface moderately glossy and densely covered with very short soft glandular hairs; average of 0.4 mm in length, NN155D in color.

*Pedicels*.—An average of 2 mm in length and 0.5 mm in diameter, 185B in color, primary flower aspect straight on top of secondary pedicel, secondary and tertiary flower aspect is 30°, moderate in strength, surface matte and moderately covered with very short soft glandular hairs an average of 0.2 mm in length and too small to measure color.

Reproductive organs:

*Gynoecium*.—Pistils; 2, 5 mm in length, stigma; club-shaped, 0.2 mm in diameter, style; an average of 4.75 mm in length and 157D in color, ovary; 145C to 145D in color.

*Androecium*.—Stamens; 5, anthers; ovate in shape, average of 0.4 mm in length and width, NN155D in color, filament; 4 mm in length and NN155D in color, pollen; moderate in quantity, 22A in color.

*Seed/fruit*.—No fruit or seeds have been observed to date.

It is claimed:

1. A new and distinct cultivar of *Heuchera* plant named 'Toncka 377' as herein illustrated and described.

* * * * *